US00RE48021E

(19) United States
(12) Reissued Patent
Fourt et al.

(10) Patent Number: US RE48,021 E
(45) Date of Reissued Patent: Jun. 2, 2020

(54) LOCK FOR AN AUTOMATIC INJECTION DEVICE

(71) Applicant: Eli Lilly and Company, Indianapolis, IN (US)

(72) Inventors: Jesse Arnold Fourt, Menlo Park, CA (US); Thomas Dieter Christian Overthun, San Francisco, CA (US); Judy Guo, San Francisco, CA (US); Thomas Gaëtan Thibault Brisebras, San Francisco, CA (US)

(73) Assignee: Eli Lilly and Company, Indianapolis, IN (US)

(21) Appl. No.: 29/674,243

(22) Filed: Dec. 20, 2018

Related U.S. Patent Documents

Reissue of:
(64) Patent No.: Des. 773,650
Issued: Dec. 6, 2016
Appl. No.: 29/530,811
Filed: Jun. 19, 2015

U.S. Applications:
(62) Division of application No. 29/672,419, filed on Dec. 5, 2018, which is an application for the reissue of Pat. No. Des. 773,650.

(51) LOC (12) Cl. ..... 24-02
(52) U.S. Cl.
USPC ..... D24/113
(58) Field of Classification Search
USPC ..... D24/112, 113, 114, 108, 127, 130, 133; D8/311; D23/252, 238
(Continued)

(56) References Cited

U.S. PATENT DOCUMENTS

D316,899 S 5/1991 Andersson et al.
D330,079 S 10/1992 Dalling et al.
(Continued)

FOREIGN PATENT DOCUMENTS

WO 2007002052 1/2007
WO 2007047200 4/2007
(Continued)

OTHER PUBLICATIONS

Ypsomed-YpsoMate® Brochure.
(Continued)

*Primary Examiner* — Philip S Hyder
(74) *Attorney, Agent, or Firm* — Marion Daniel Spillman

(57) CLAIM

The ornamental design for *a lock for* an automatic injection device, as shown and described.

DESCRIPTION

[FIG. 1 is a top perspective view of an automatic injection device showing our new design;]
[FIG. 2 is a bottom perspective view thereof:]
[FIG. 3 is a front view thereof;]
[FIG. 4 is a rear view thereof;]
[FIG. 5 is side view thereof;]
[FIG. 6 is an opposite side view thereof;]
[FIG. 7 is a top view thereof; and,]
[FIG. 8 is a bottom view thereof.]
*FIG. 9 is a top perspective view of the lock for an automatic injection device showing our new design;*
*FIG. 10 is a bottom perspective view thereof;*
*FIG. 11 is a front view thereof;*
*FIG. 12 is a rear view thereof;*
*FIG. 13 is side view thereof;*
*FIG. 14 is an opposite side view thereof;*
*FIG. 15 is a top view thereof; and,*
*FIG. 16 is a bottom view thereof.*
[The small ovals in the central height region of FIGS. 1-6 show projecting texturing that form part of the claimed design.] The broken lines showing internal portions and a
(Continued)

*(New)* bottom portion of the *lock for an* automatic injection device form no part of the claimed design.

1 Claim, 10 Drawing Sheets

Matter enclosed in heavy brackets [ ] appears in the original patent but forms no part of this reissue; matter printed in italics indicates the additions made by reissue.

(58) Field of Classification Search
CPC ..... A61M 5/178; A61M 3/00; A61M 5/20; A61M 5/31; A61M 5/3146; A61M 5/3129; A61M 5/3148; A61M 5/315
See application file for complete search history.

(56) References Cited

U.S. PATENT DOCUMENTS

| | | | | | |
|---|---|---|---|---|---|
| D420,739 | S | | 2/2000 | Moreau-Defarges | |
| D428,640 | S | * | 7/2000 | Pitsch | D23/238 |
| D461,555 | S | * | 8/2002 | Binet | D24/114 |
| D471,976 | S | | 3/2003 | Pavlu et al. | |
| D476,078 | S | | 6/2003 | Pavlu et al. | |
| D476,734 | S | | 7/2003 | Pavlu et al. | |
| D483,116 | S | | 12/2003 | Castellano | |
| D531,702 | S | * | 11/2006 | Haug | D23/252 |
| D607,558 | S | * | 1/2010 | Abry | D24/113 |
| D628,690 | S | | 12/2010 | Galbraith | D24/114 |
| 7,918,824 | B2 | | 4/2011 | Bishop et al. | |
| D652,136 | S | * | 1/2012 | Hawley | D24/113 |
| D655,595 | S | * | 3/2012 | Ouellette | D8/311 |
| D669,397 | S | * | 10/2012 | Isokari | D12/110 |
| D670,375 | S | | 11/2012 | Corbin | |
| D670,376 | S | | 11/2012 | Corbin | |
| D677,380 | S | | 3/2013 | Julian et al. | |
| 8,409,138 | B2 | | 4/2013 | James et al. | |
| D690,416 | S | * | 9/2013 | Cappello | D24/112 |
| D695,892 | S | * | 12/2013 | Cappello | D24/113 |
| D696,397 | S | | 12/2013 | Guarraia et al. | |
| D708,317 | S | | 7/2014 | Schneider et al. | |
| D714,932 | S | * | 10/2014 | Hall | D24/112 |
| D721,802 | S | * | 1/2015 | Ohashi | D24/113 |
| D722,158 | S | * | 2/2015 | Magome | D24/113 |
| D724,721 | S | | 3/2015 | Geert-Jensen et al. | |
| D728,782 | S | | 5/2015 | Dubuc et al. | |
| D729,930 | S | | 5/2015 | Geert-Jensen et al. | |
| D732,161 | S | * | 6/2015 | Ohashi | D24/113 |
| D739,011 | S | * | 9/2015 | Morrison, Jr. | D24/114 |
| D741,472 | S | * | 10/2015 | Yotani | D24/108 |
| D743,560 | S | * | 11/2015 | Pietrantonio | D24/186 |
| D747,476 | S | * | 1/2016 | Kawamura | D24/130 |
| D747,797 | S | * | 1/2016 | Fourt | D24/114 |
| D748,270 | S | * | 1/2016 | Pietrantonio | D24/186 |
| D748,746 | S | * | 2/2016 | Eder | D21/694 |
| D758,570 | S | * | 6/2016 | Wohlfahrt | D24/113 |
| D758,826 | S | * | 6/2016 | Geyer | D8/311 |
| D770,610 | S | * | 11/2016 | Saussaye | D24/113 |
| D777,908 | S | * | 1/2017 | Amend Kwasnik | D24/113 |
| D780,909 | S | * | 3/2017 | Burkett | D24/113 |
| D785,781 | S | * | 5/2017 | Chan | D24/112 |
| 2011/0092915 | A1 | | 4/2011 | Olson et al. | |
| 2015/0260745 | A1 | * | 9/2015 | Chan | G01N 35/10 73/61.59 |

FOREIGN PATENT DOCUMENTS

| | | |
|---|---|---|
| WO | 2010104779 | 9/2010 |
| WO | 2011109205 | 9/2011 |
| WO | 2013032779 | 3/2013 |
| WO | 2014062488 | 4/2014 |

OTHER PUBLICATIONS

Schreiner Group—New Labels with Tamper-Evident and Non-Slip Features Help Enhance Patient Safety(URL: http://www.schreiner-group.com/3/company/press-room/schreiner-medipharm-us/new-labels-with-tamper-evident-and-non-slip-features-help-enhance-patient-safety/).

Unpublished Design U.S. Appl. No. 29/449,492, Eli Lilly and Company, entitled "Automatic Injection Device" filed Mar. 15, 2013.

* cited by examiner

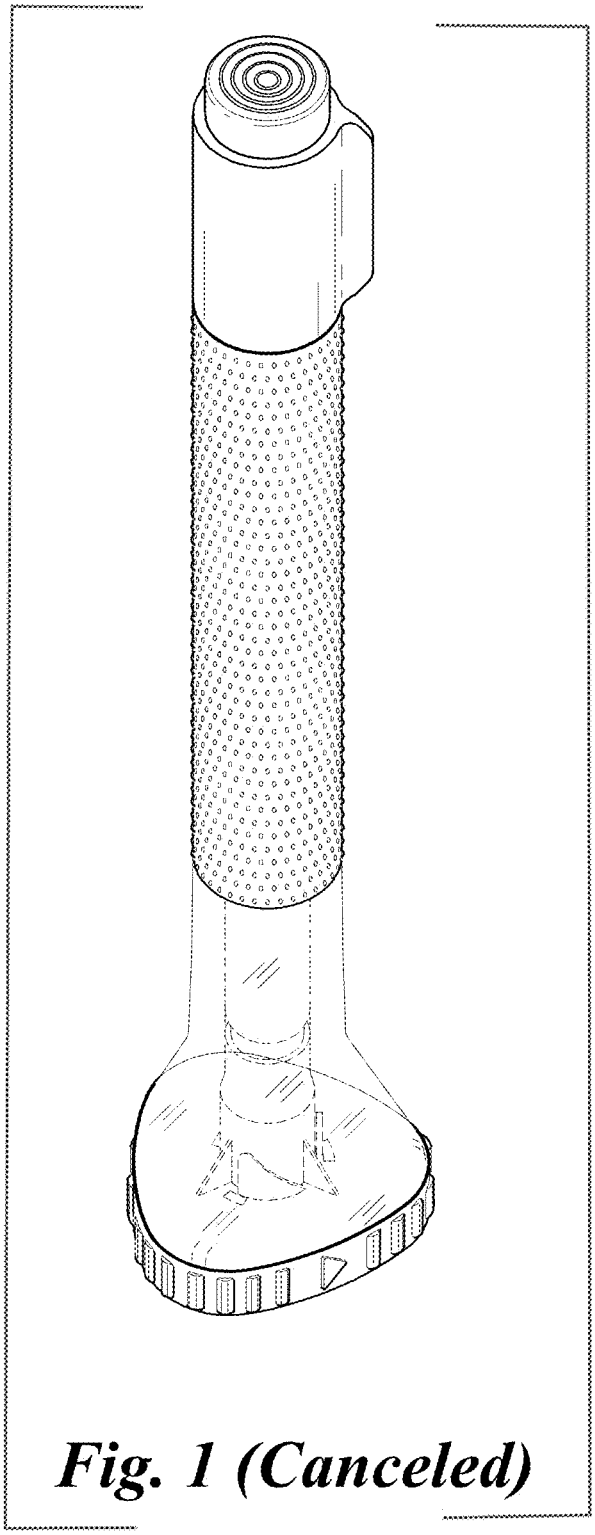
*Fig. 1 (Canceled)*

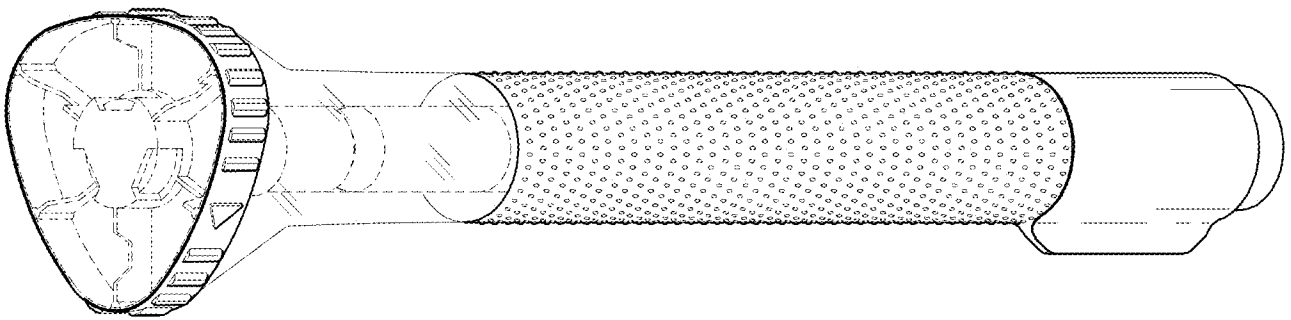
*Fig. 2 (Canceled)*

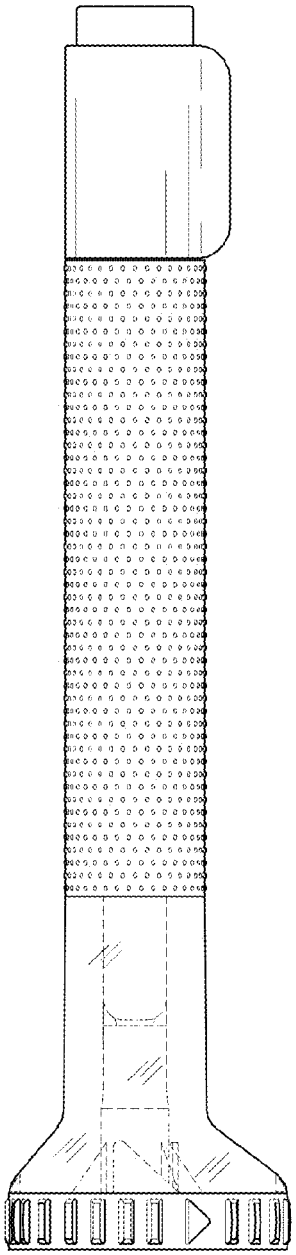
*Fig. 3 (Canceled)*
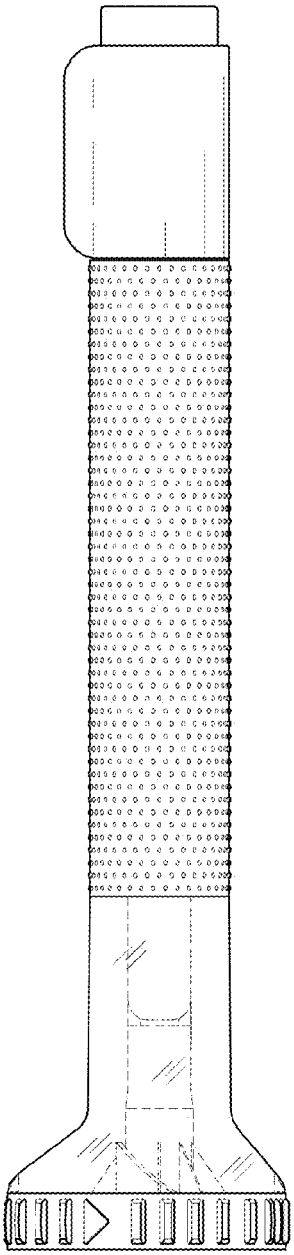
*Fig. 4 (Canceled)*

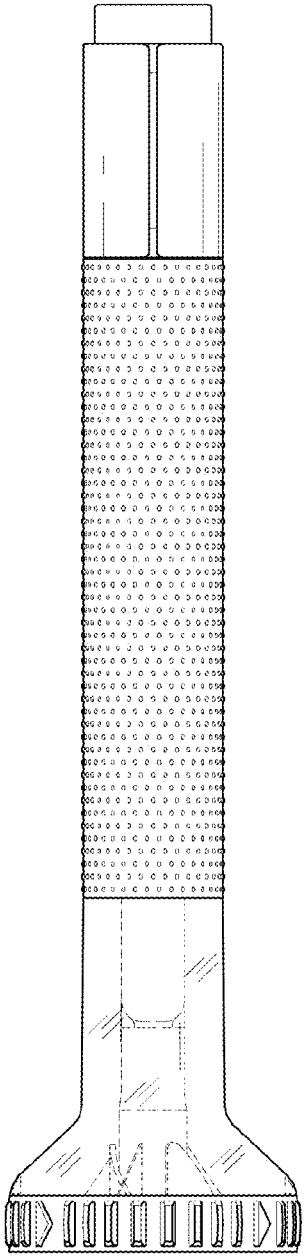
*Fig. 5 (Canceled)*
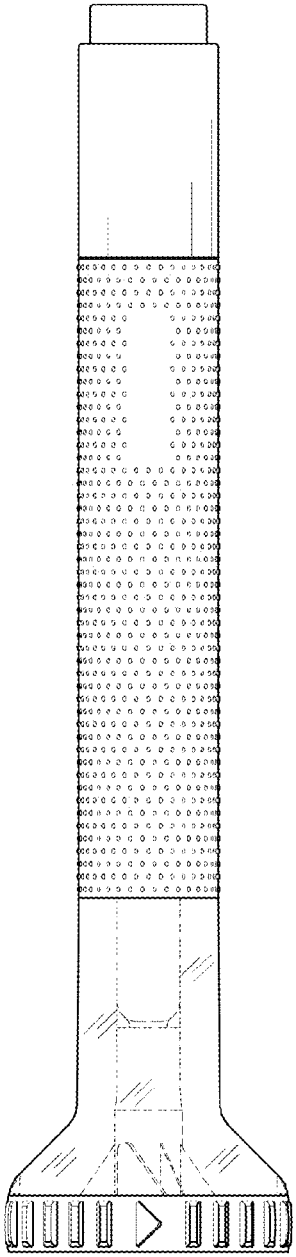
*Fig. 6 (Canceled)*

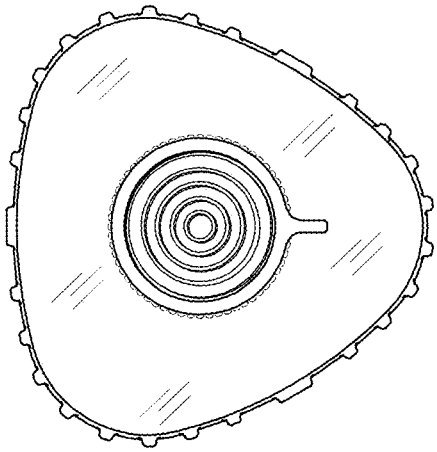
*Fig. 7 (Canceled)*
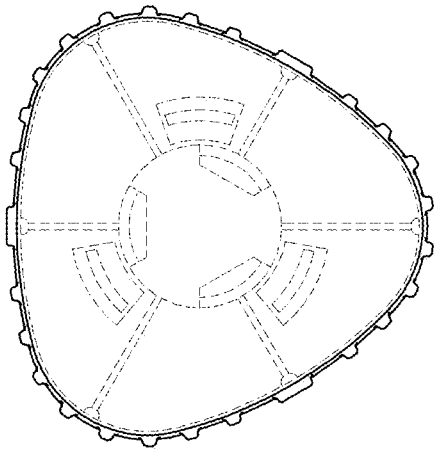
*Fig. 8 (Canceled)*

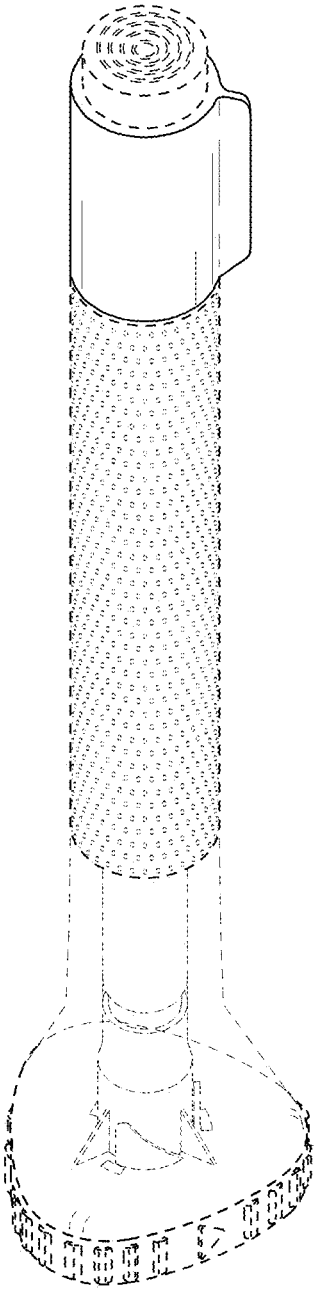
*Fig. 9 (New)*

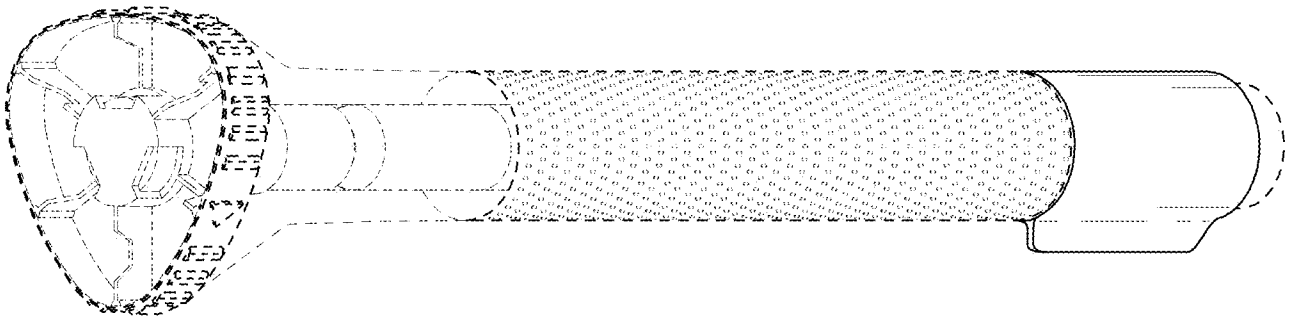
*Fig. 10 (New)*

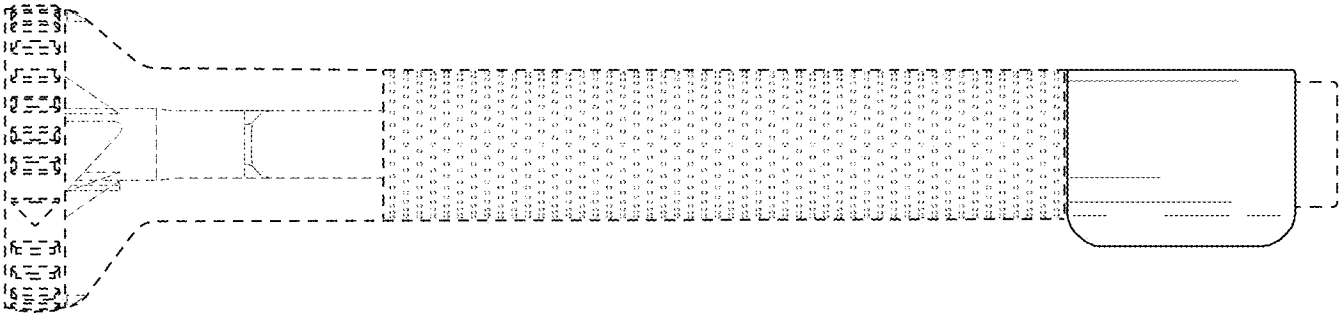
*Fig. 11 (New)*
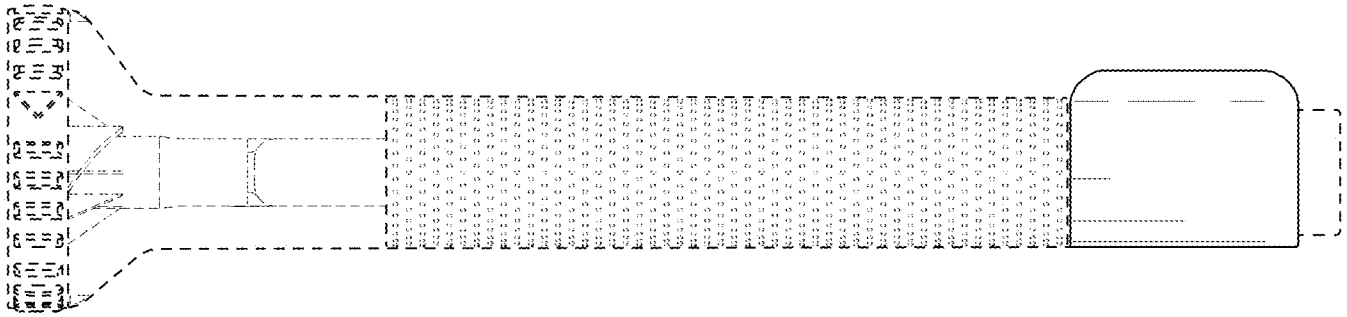
*Fig. 12 (New)*

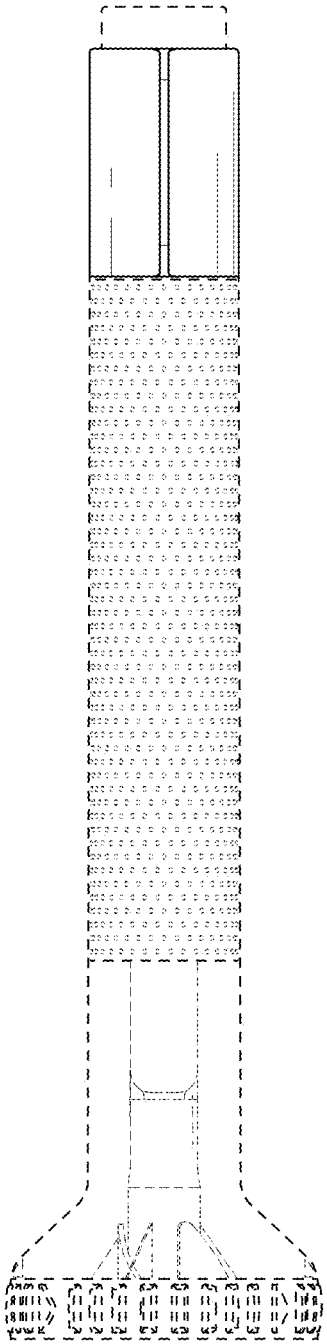
*Fig. 13 (New)*
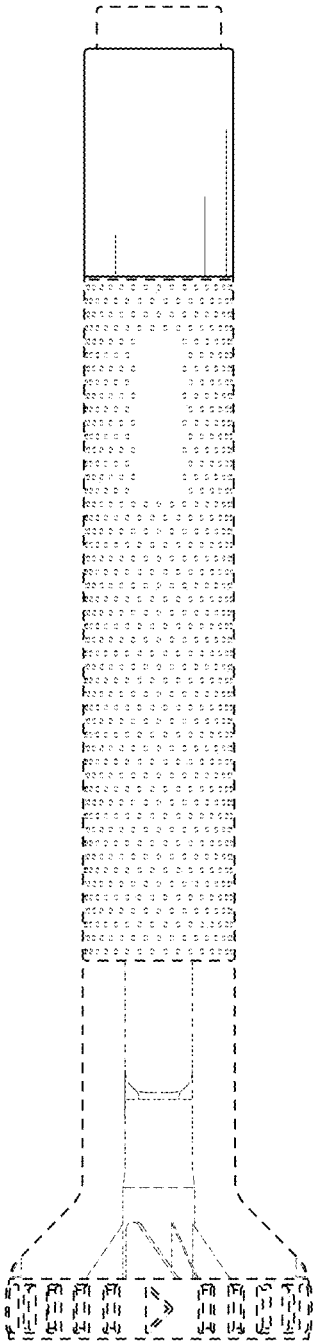
*Fig. 14 (New)*

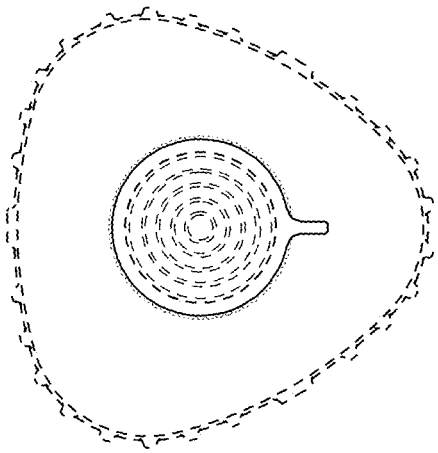
*Fig. 15 (New)*
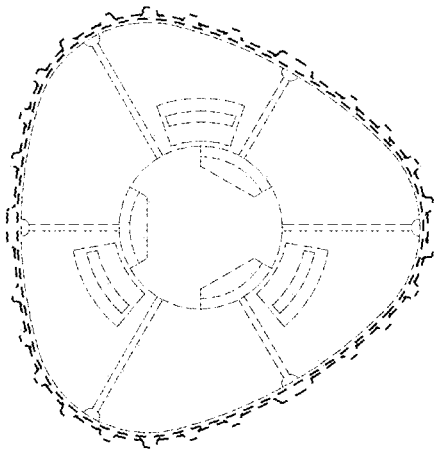
*Fig. 16 (New)*